US010952818B2

(12) United States Patent
Brady

(10) Patent No.: US 10,952,818 B2
(45) Date of Patent: Mar. 23, 2021

(54) DENTAL/ORTHODONTIC ASSEMBLY

(71) Applicant: William B. Brady, Newport Beach, CA (US)

(72) Inventor: William B. Brady, Newport Beach, CA (US)

(*) Notice: Subject to any disclaimer, the term of this patent is extended or adjusted under 35 U.S.C. 154(b) by 620 days.

(21) Appl. No.: 15/356,356

(22) Filed: Nov. 18, 2016

(65) Prior Publication Data

US 2017/0312053 A1 Nov. 2, 2017

Related U.S. Application Data

(60) Provisional application No. 62/329,513, filed on Apr. 29, 2016.

(51) Int. Cl.
*A61C 7/06* (2006.01)
*A61F 5/055* (2006.01)

(52) U.S. Cl.
CPC .............. *A61C 7/065* (2013.01); *A61F 5/055* (2013.01)

(58) Field of Classification Search
CPC ................................ A61C 7/065; A61F 5/055
USPC ........................................................... 433/5
See application file for complete search history.

(56) References Cited

U.S. PATENT DOCUMENTS

| 2,334,894 A | 11/1943 | Atkinson | |
| 2,735,424 A * | 2/1956 | Benjamin | A61F 5/055 602/17 |
| 3,036,380 A * | 5/1962 | Martinek | A61C 7/06 433/5 |
| 4,577,627 A * | 3/1986 | Facal Garcia | A61C 7/06 433/5 |
| 4,987,891 A * | 1/1991 | Gaylord, Jr. | A61F 5/055 128/DIG. 23 |
| 4,988,291 A | 1/1991 | Grummons | |
| 5,810,583 A | 9/1998 | Doyle | |
| 5,890,891 A * | 4/1999 | Doyle | A61C 7/06 433/5 |
| 6,976,838 B1 | 12/2005 | Keles | |
| 2013/0052602 A1* | 2/2013 | Bukhary | A61C 7/065 433/5 |

FOREIGN PATENT DOCUMENTS

WO  WO 1997/031584 A1  1/1997
WO  WO 2001/043657    6/2001

OTHER PUBLICATIONS

The CRANE, 3 pages, https://web.archive.org/web/20151127143814/http://www.thecranerp.com/, dated as available on Nov. 27, 2015 by the Wayback Machine internet archive (accessed and printed on Aug. 25, 2020).

(Continued)

*Primary Examiner* — Yogesh P Patel
(74) *Attorney, Agent, or Firm* — Knobbe, Martens, Olson & Bear, LLP

(57) ABSTRACT

Systems for dental/orthodontic treatment can include a cervical collar, a brace, a mount, and an upper support. The brace can extend from an anterior section of the cervical collar to the upper support, which can be positioned to engage a forehead of a dental/orthodontic treatment patient. The mount can be engaged to and positioned on the brace, and can be configured to receive one or more elastics extending from fixation points within the mouth of the patient.

11 Claims, 4 Drawing Sheets

(56) References Cited

OTHER PUBLICATIONS

About the CRANE, 2 pages, https://web.archive.org/web/20151127133950/http://www.thecranencrp.com/aboutthecrane.html, dated as available on Nov. 27, 2015 by the Wayback Machine internet archive (accessed and printed on Aug. 25, 2020).

How to Wear the Crane, 3 pages, https://web.archive.org/web/20151127145136/http://www.thecranencrp.com/howtowear.html, dated as available on Nov. 27, 2015 by the Wayback Machine internet archive (accessed and printed on Aug. 25, 2020).

The Bow, 3 pages, https://web.archive.org/web/20180722232523/http://www.forwardontics.com/bow.html, dated as available on Jul. 22, 2018 by the Wayback Machine internet archive (accessed and printed on Aug. 25, 2020).

\* cited by examiner

DENTAL/ORTHODONTIC ASSEMBLY

INCORPORATION BY REFERENCE TO ANY PRIORITY APPLICATIONS

This application claims the benefit of U.S. Provisional Application No. 62/329,513, filed Apr. 29, 2016, the entirety of which is hereby incorporated by reference herein for all purposes.

BACKGROUND

Field

The present disclosure relates to dental/orthodontic treatment systems, methods, and apparatuses, and more particularly, in some arrangements, relates to extraoral dental/orthodontic assemblies and methods of use thereof.

Description of the Related Art

Orthodontic headgear is used to treat dental/orthodontic issues including overbites, overjets, underbites, negative overjets, malocclusion, and the like. Underbites are typically treated using facemask or reverse-pull headgear, which apply a pulling force to a patient's maxilla in an anterior direction. Devices for treating an underbite can include a face frame that fits over and is stabilized on a patient's face and one or more straps fitted around the patient's head.

SUMMARY

Certain embodiments of the present disclosure are directed to a dental/orthodontic treatment system. The dental/orthodontic treatment system can include a cervical collar; a brace secured to an anterior section of the cervical collar, the brace configured to extend from the cervical collar in a direction of an oral cavity of a patient, a mount securably coupled to the brace, and one or more elastics configured to engage the mount, wherein the one or more elastics are configured to extend from the mount to one or more fixation points within the oral cavity of the patient, wherein the one or more elastics are configured to exert a force on the one or more fixation points within the oral cavity of the patient.

Certain embodiments of the present disclosure are directed to a dental/orthodontic assembly that can include a brace configured to extend from a fixation point adjacent to a chin of a patient to a location above an oral cavity of the patient, a mount configured to slidably engage the brace, wherein the mount is configured to slide along a length of the brace when the mount is in an unsecured configuration, wherein the mount comprises a plurality of grooves extending laterally along a length of the mount, the one or more grooves configured to engage one or more elastics secured to a location within the oral cavity of the patient, a fastener configured to engage the mount and the brace, wherein the fastener is configured to secure the mount to the brace when in a secured configuration and to allow movement of the mount along the brace when in an unsecured configuration, and a support secured to an upper end of the brace, wherein the support is configured to engage a surface of a forehead of the patient, wherein fixation of the brace to the fixation point below the oral cavity and engagement of the support to the forehead of the patient provide for fixation of the brace with respect to the patient in at least one direction.

Certain embodiments of the present disclosure are directed to a method for providing a dental/orthodontic treatment. The method can include fixing a brace to fixation point at an anterior section of a cervical collar positioned on a patient, wherein the brace is configured to extend from the cervical collar in a direction of an oral cavity of the patient, securing a mount to the brace, and coupling one or more elastics to the mount, wherein the one or more elastics are configured to extend from the mount to one or more fixation points within the oral cavity of the patient, wherein the one or more elastics are configured to exert a force on the one or more fixation points within the oral cavity of the patient.

DETAILED DESCRIPTION OF THE PREFERRED EMBODIMENTS

Figure 1:
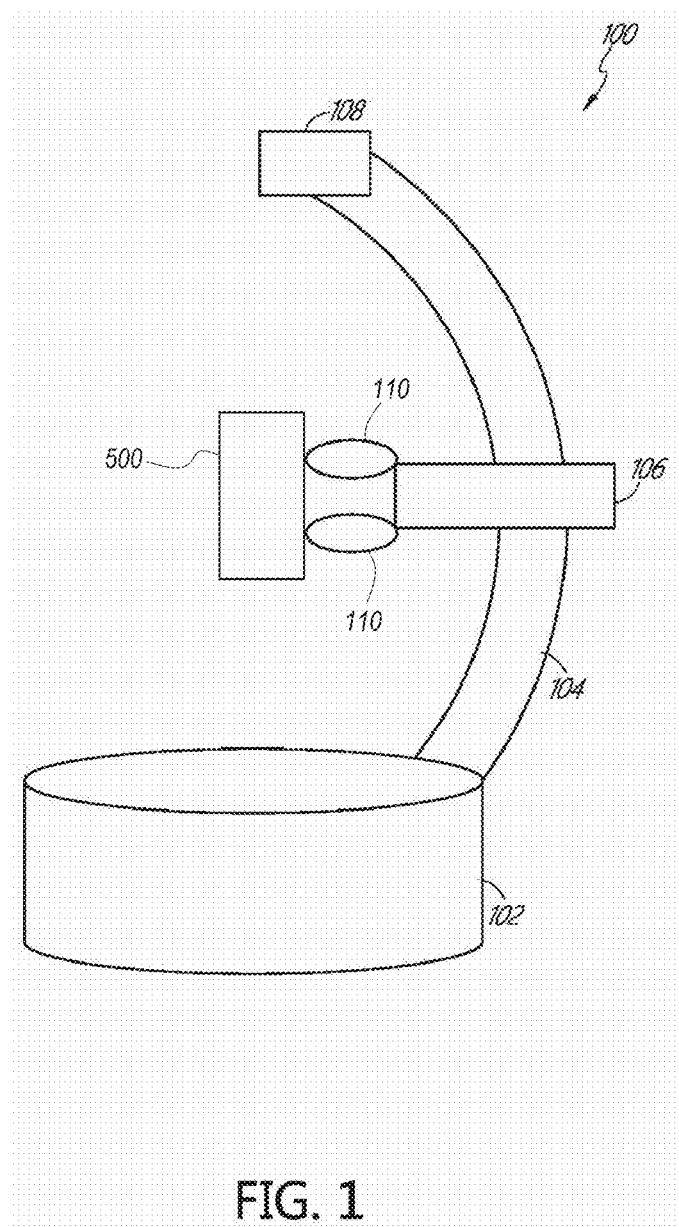
FIG. 1 depicts a schematic view of a dental/orthodontic assembly in accordance with an illustrative embodiment.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments. In addition, embodiments of the inventions can comprise several novel features and no single feature is solely responsible for its desirable attributes or is essential to practicing the inventions herein described.

Although certain aspects, advantages, and features are described herein, it is not necessary that any particular embodiment include or achieve any or all of those aspects, advantages, and features. Some embodiments may not achieve the advantages described herein, but may achieve other advantages instead. Any structure, feature, or step in any embodiment can be used in place of, or in addition to, any structure, feature, or step in any other embodiment, or omitted. This disclosure contemplates all combinations of features from the various disclosed embodiments. No feature, structure, or step is essential or indispensable.

The present disclosure includes embodiments of extraoral dental/orthodontic treatment methods and apparatuses. The methods and apparatuses for some embodiments are particularly useful for treatment of underbites and/or malocclusions.

Some aspects of the present disclosure include an extraoral dental/orthodontic assembly, which can be configured to apply a force in one or more directions to one or more teeth or bones of a dental/orthodontic patient.

The dental/orthodontic assembly can include one or more elastics or other force generating members, which can be configured to engage with, or be structurally coupled to, a dental/orthodontic treatment area or fixation point within the oral cavity of a patient, such as one or more teeth of the upper or lower jaw, the maxilla, mandible, and/or any other bone used for orthodontic treatment of the patient. In some embodiments, the elastics or other force generating members can be configured to engage with, or be structurally coupled to, fixation points of one or more dental/orthodontic implants or devices secured to the teeth or bone of the patient. The elastics or other force generating members can be configured to apply a force to a dental/orthodontic treatment area in one or more directions in order to facilitate movement of one or more teeth or bones, and/or to facilitate or inhibit growth of the upper and/or lower jaw.

The elastics or other force generating members can be engaged with, or structurally coupled to, a mount, which can be positioned to apply a force to the elastics or other force generating members, such that the elastics or other force generating members apply a force to a dental/orthodontic treatment area. For example, the mount can be positioned such that when an elastic is engaged with the mount and a fixation point of a dental/orthodontic treatment area, the elastic is tensioned, and the tension of the elastic generates a force on the dental/orthodontic treatment area. The mount can include one or more hooks, fasteners, grooves, or other attachment members for receiving and/or securing one or more elastics or other tension generating members.

The mount can be engaged with, or structurally coupled to, a brace that is secured in a fixed or semi-fixed position relative to the body of a patient. The brace can be positioned with respect to the body of the patient such that the mount, when engaged with the brace, is positioned at a distance from a dental/orthodontic treatment area that can cause tension in an elastic or other force generating member. The mount may be adjustable to a plurality of positions along the length of the brace to facilitate forces on a dental/orthodontic treatment area in a plurality of directions. For example, in some embodiments, the brace may be shaped as a pole extending from a lower position beneath the oral cavity of a patient to an upper position above the oral cavity of the patient, and the mount can be vertically adjusted to a plurality of positions along the length of the pole.

The brace can be attached at one or more fixation points. In some embodiments, a lower end of the brace can be secured to a cervical collar or neck brace, which can have a shape and size for fitting around and providing support to a patient's neck. The collar can be a rigid collar or soft collar. A rigid collar can provide increased support, while a soft collar can provide more flexibility. The collar can include an outer shell made of a rigid material, such as, for example, one or more rigid plastics. The collar can further include one or more interior sections including a padded material, which can increase patient comfort. In some embodiments, a dental/orthodontic treatment apparatus can include a commercially available cervical collar. The cervical collar can be positioned and secured such that one or more portions of the cervical collar are relatively fixed with respect to the position of a patient's head. Consequently, the brace can be secured to the collar such that the brace is maintained in a relatively stabilized and fixed position with respect to the oral cavity of the patient. The collar can also provide support to the neck and/or head of the patient. For example, the collar can provide support to the chin of the patient.

In some embodiments, the brace can be secured to a cervical collar at a position adjacent to or directly below the chin of a patient. A brace positioned adjacent to or directly below the chin of a patient may provide several advantages over a brace secured to alternative locations on a cervical collar, such as locations on the cervical collar positioned over the chest or torso of the patient. A brace secured to a position over the chest or torso of a patient may apply undesired pressure to the patient's chest causing discomfort, or may provide a less stable point of attachment, requiring several additional points of fixation. A brace secured to a position over the chest may also be more obtrusive and extend farther away from the patient as compared to brace secured to a cervical collar at a position adjacent to or directly below the chin of a patient.

The dental/orthodontic assembly can further include an upper support attached to an upper end of the brace which can be positioned against a surface on the head of the patient (e.g., the patient's forehead) to provide increased stability and support. For example, the upper support may be positioned on the forehead of a patient. In some embodiments, the upper support is provided in addition to fixation at the lower end of the brace at one or more fixation points, for example, fixation to a cervical collar. An advantage of providing an upper support in addition to the cervical collar, or other device providing fixation at the lower end of the brace, is that the cervical collar, or other device providing fixation at the lower end of the brace, need not be as bulky and stiff as compared to an arrangement that relied solely on the cervical collar, or other device providing fixation at the lower end of the brace, for support. Accordingly, with an upper support and a cervical support of the brace, or other device providing fixation at the lower end of the brace, a less bulky and typically less expensive conventional neck brace or cervical collar can be used in certain embodiments.

FIG. 1 depicts a schematic view of a dental/orthodontic assembly 100 in accordance with an illustrative embodiment of the present disclosure. The dental/orthodontic assembly can include a collar 102, a brace 104, a mount 106, an upper support 108, and a plurality of elastics 110. The collar 102 can be configured to engage the neck of a patient. In some embodiments, the collar 102 is configured to at least partially encircle the neck of a patient. In some embodiments, the collar 102 can be configured to restrict movement of the neck and/or head of the patient in one or more directions, such as, for example, flexion and extension of the neck. The collar 102 can restrict movement of the neck/and or head such that the head of the patient is in a fixed or semi-fixed position relative to at least one portion of the collar 102 in at least one direction. In certain embodiments, the collar 102 can comprise a conventional neck brace or cervical collar that is used to treat neck or cervical injuries. The elastics 110 can comprise conventional elastics such as elastic rubber bands.

A lower end of the brace 104 can be secured to the collar 102. In some embodiments, the lower end of the brace 104 is secured to the collar 102 such that the brace 104 is stabilized or at least partially stabilized in a fixed position relative to the head and/or oral cavity of the patient in at least one direction.

An upper end of the brace 104 can be secured to the upper support 108. The upper support 108 can be configured to engage a surface of the patient's head or face, such as, for example, the patient's forehead. The brace 104 can be shaped such that the upper support 108 is positioned to engage a surface of the patient's head or face when the brace 104 is secured to the collar 102. Engagement of the upper support 108 with a surface of the patient's head or face can provide additional support and/or stability to the brace 104. The upper support 108 may include one or more padded sections on a face of the upper support 108 that engages the forehead of the patient. The padded surface may limit patient discomfort. In some embodiments, the face of the upper support 108 that engages the forehead of the patient may also be configured to provide friction. In some embodiments, friction provided by the face of the upper support 108 limits movement of the upper support 108 and brace 104 with respect to the forehead of the patient. In the illustrated embodiment, the brace 104 can have a curved shaped such that the mount 106 is generally further away (with respect to the patient) than the upper support 108 and a connection of the brace 104 to the collar 102.

The mount 106 can engage the brace 104. In some embodiments, the mount 106 is moveable along the brace 104 to a plurality of different positions at which the mount 106 can be secured. For example, the mount 106 may include a hole or slot through which the brace 104 can extend, and the mount 106 may be slidable along the brace 104. In some embodiments, the mount 106 is affixed to a single position on the brace 104 or can be integrally formed with the brace 104. The mount 106 can be secured to the brace 104 in a variety of manners such as set screws, thumb screws, levers, etc.

The elastics 110 can be securably engaged to the mount 106. The mount 106 can include one or more hooks, grooves, holes, or other receiving members for engaging the elastics 110. Each elastic 110 can be configured to securably couple to a fixation point 500 of a dental/orthodontic treatment area of the patient or dental/orthodontic treatment implant or device of the patient. For example, each elastic 110 can be configured to couple to one or more teeth of the upper or lower jaw, or bone in the upper or lower jaw. Each elastic 110 may also be configured to couple with a hook, groove, hole, or other receiving member of an implant or dental/orthodontic device, such as dental/orthodontic braces, within the mouth of the patient.

Figure 2:
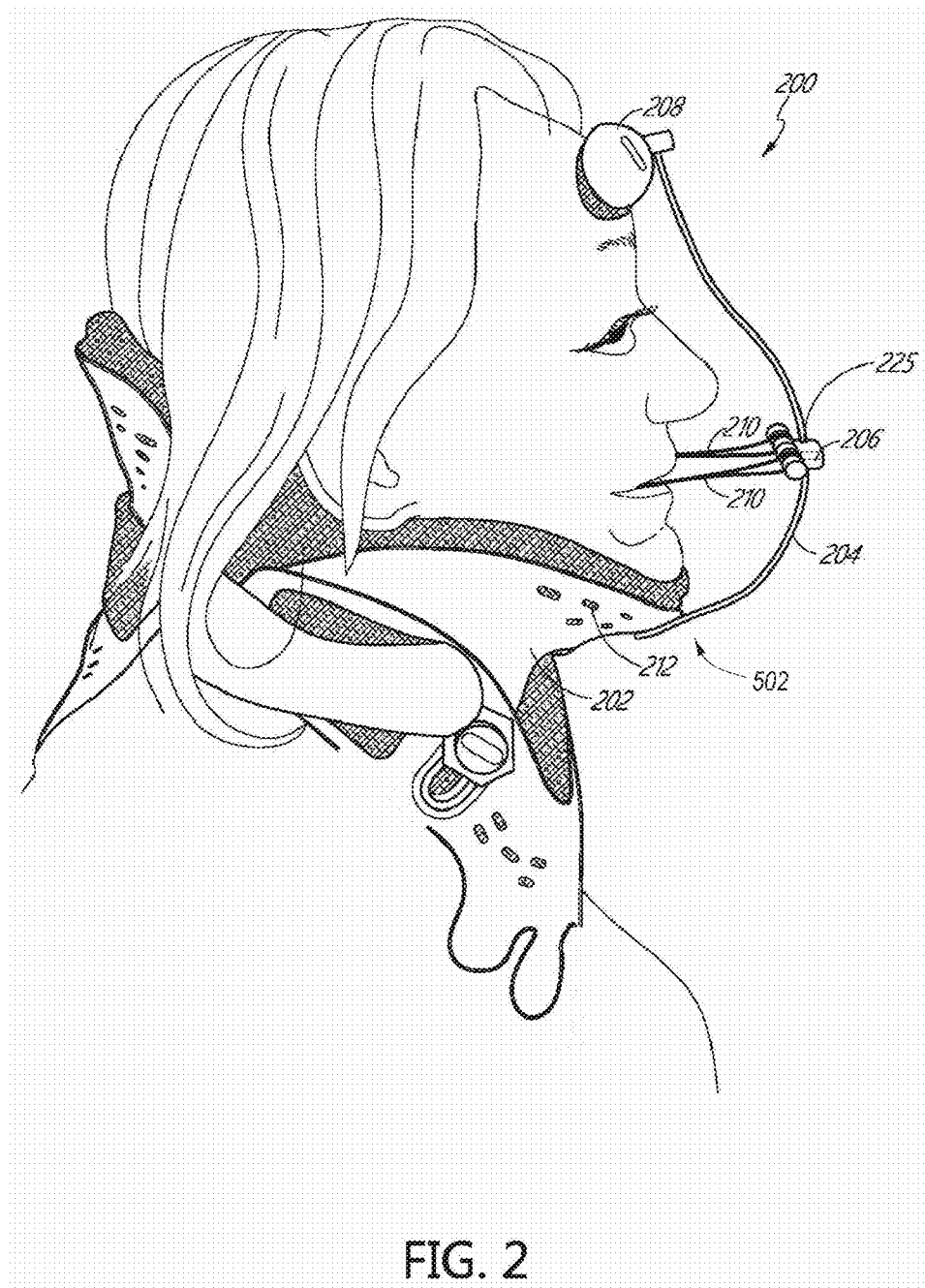
FIG. 2 depicts a side view of a dental/orthodontic assembly being worn by a dental/orthodontic patient in accordance with an illustrative embodiment.

FIG. 2 depicts a side view of an dental/orthodontic assembly 200 being worn by a dental/orthodontic patient in accordance with an illustrative embodiment. Similar to the embodiment described above, the dental/orthodontic assembly can include a collar 202, a brace 204, a mount 206, an upper support 208, and a plurality of elastics 210. The collar 222 can be configured to engage the neck of a patient. In some embodiments, the collar 202 is configured to at least partially encircle the neck of a patient. In some embodiments, the collar 202 can be configured to restrict movement of the neck and/or head of the patient in one or more directions, such as, for example, flexion and extension of the neck. The collar 202 can restrict movement of the neck/and or head such that the head of the patient is in a fixed or semi-fixed position relative to at least one portion of the collar 202 in at least one direction. In certain embodiments, the collar 202 can comprise a conventional neck brace or cervical collar that is used to treat neck or cervical injuries. The elastics 210 can comprise conventional elastics such as elastic rubber bands.

In this embodiment of FIG. 2, the collar 202 includes an anterior section 212 that extends below the chin of the patient. The anterior section 212 can provide support to the chin of the patient. The lower end of the brace 204 can be securably coupled with the anterior section 212 of the collar 202 at a fixation point 502.

In the illustrated embodiment, the upper support 208 is positioned against the forehead of the patient. The brace 204 can be a curved pole extending from the anterior portion 212 of the collar 202 to the upper support 208. The brace 204 can be curved such that a middle section of the brace 204 is positioned anterior to the anterior section 212 of the neck brace 202 and the upper support 208. The upper support 208 can be provided with padding identified by hatching in FIG. 2, which can extend between the upper support 208 and the forehead of the patient.

Figure 3:
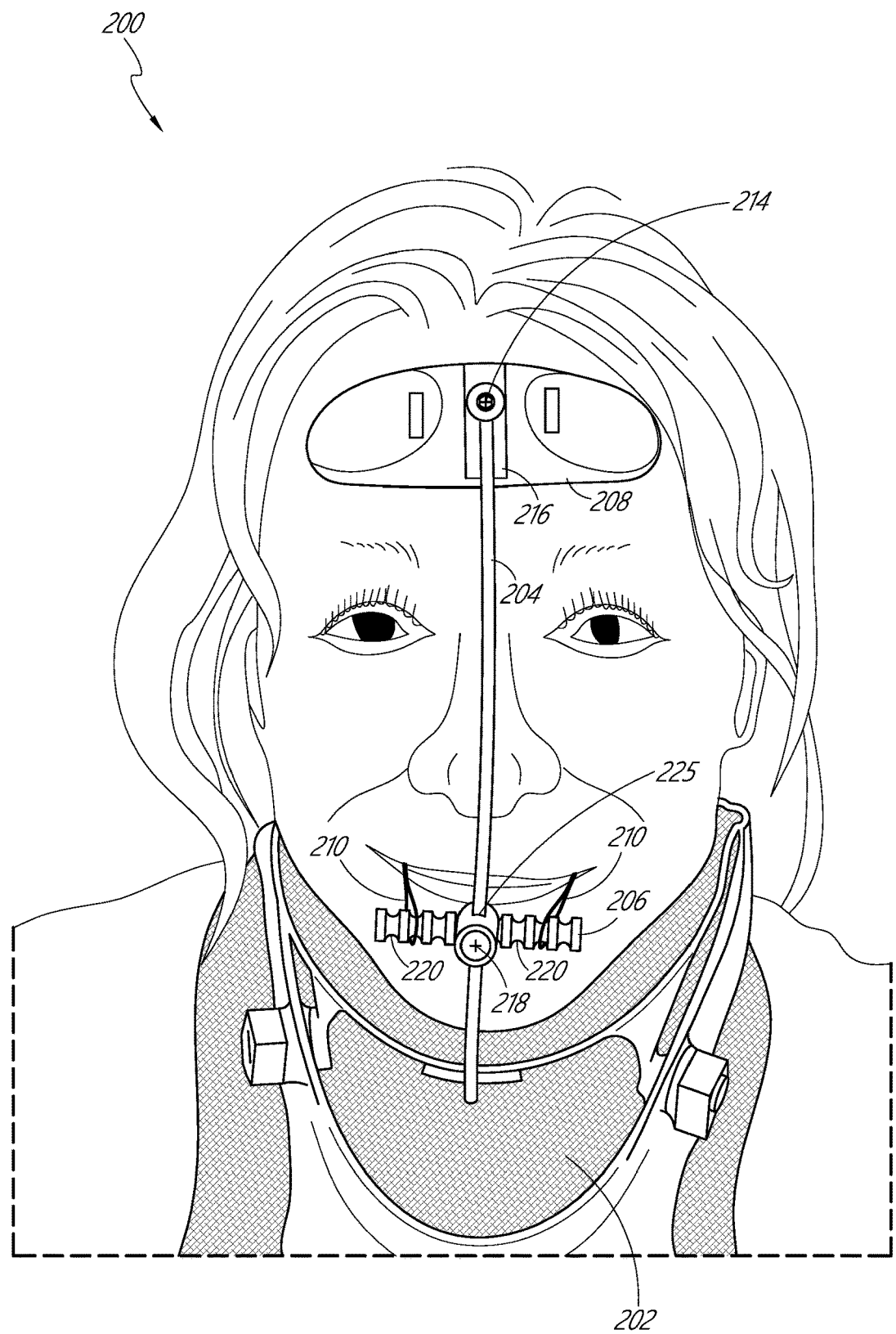
FIG. 3 depicts a front view of a dental/orthodontic assembly being worn by a dental/orthodontic patient in accordance with an illustrative embodiment.

FIG. 3 depicts a front view of the dental/orthodontic assembly 200 of FIG. 2 being worn by a dental/orthodontic patient in accordance with an illustrative embodiment. As shown, the brace 204 can be secured to the upper support 208 by a fastener 214. The fastener 214 can include a threaded fastener, a hook, a strap, or any other type of fastener. In alternative embodiments, the brace 204 can be integrally formed with the upper support 208. The upper support 208 can further include a groove 216 that can be configured to align with and/or receive the brace 204 and/or fastener 214.

The mount 206 can be securably coupled to the brace 104 by a fastener 218. The fastener 218 can include a threaded fastener, a hook, a strap, or any other type of fastener. In some embodiments, the mount 206 is configured to be slidable along the brace 204 when the fastener 218 is removed or loosened. In such embodiments, the mount 206 can include a groove or hole 225 through which the brace 204 can extend. The mount 206 can be securably coupled to a plurality of locations along the brace 204 by sliding the mount 206 along the brace and tightening the fastener 218. In some embodiments, the mount 206 is configured to be removable from the brace 204 when the fastener 218 is removed and can be securably coupled to a plurality of locations along the brace 204 by positioning the mount 206 in alignment with one of the plurality of locations and coupling the fastener 218 to the mount 206. In some embodiments, the fastener 218 extends through an anterior face of the mount 206 towards an anterior surface of the brace 204. The brace 204 can include one or more holes for receiving the fastener 218. Alternatively, the fastener 218 can engage the brace 204 through an interference fit. Changing the position of the mount 206 along the brace 204 can allow for different forces on the treatment area or dental/orthodontic implant or device by the elastics 210.

The mount 206 can include a plurality of grooves 220 configured to receive the elastics 210. The mount 206 can extend laterally outward from the brace 204. The grooves 220 can be positioned on the mount 206 such that elastics 210 can engage the mount at a plurality of lateral positions along the length of the mount 206. Alternatively, the mount 206 can include one or more hooks or other suitable structures for receiving the elastics 210.

One or more fasteners (not shown) can also secure the brace 204 to the anterior section 212 of the collar 202. The fasteners can include a threaded fastener, a hook, a strap, adhesive, or any other type of fastener. The brace 204 can be securably coupled to a rigid portion of the collar 202. The collar 202 may include one or more rigid portions on the exterior of the collar 202 to provide stability and support. The collar 202 may further include one or more padded interior sections, which can limit patient discomfort. Such padded interior sections are identified by hatching in FIGS. 2-4. The collar 202 can be configured to provide support to the neck and chin of the patient in addition and to provide support and stabilization to the brace 204.

Fixation of the brace 204 to the anterior section 212 of the collar 202 can provide several advantages over conventional headgear apparatuses. For example, fixation of the brace 204 to the anterior section 212 of the collar 202 allow for stabilization of the brace 204 with respect to the oral cavity of the patient without exerting excess pressure on other segments of the body, such as the chest. Further, the collar 202 can be a conventional cervical collar, which can eliminate the need for more expensive and/or bulky specialized equipment. The positioning of the brace 204 on the anterior section 212 can also provide for support such that the upper support 208 can provide for stabilization without the requirement of an additional strap or band. Further, the attachment of the brace 204 to the anterior section 212 below the chin can provide for a minimal length of the brace 204, which can reduce the area over which the brace 204 interferes with other body movement, such as movement of the arms, when positioned over the chest.

The brace 204 can be positioned such that the brace 204 is generally laterally aligned with the center of the patient's face. For example, the brace 204 can be positioned between the eyes of the patient to allow for visibility while wearing the dental/orthodontic apparatus 200.

Figure 4:
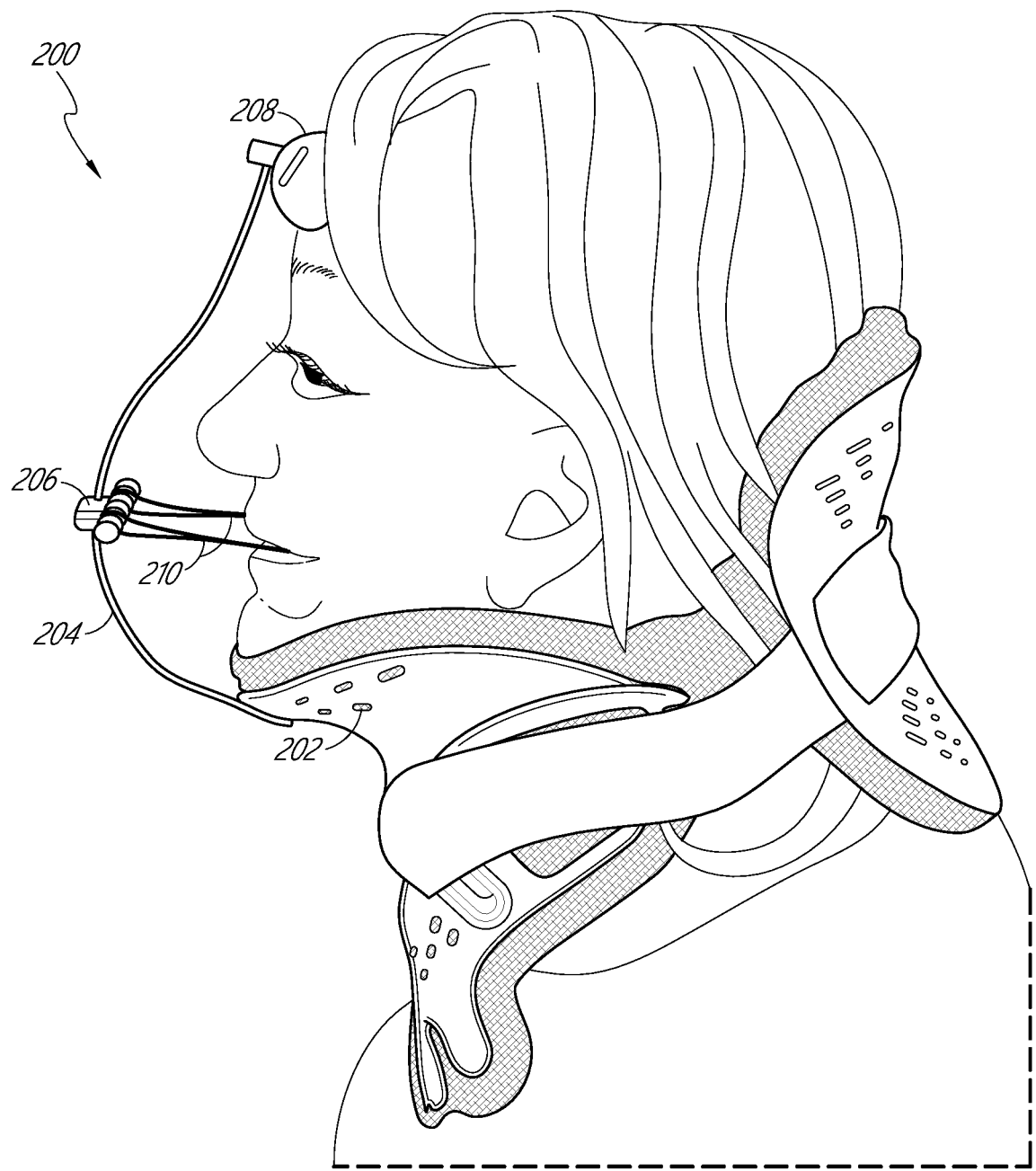
FIG. 4 depicts a side view of a dental/orthodontic assembly being worn by a dental/orthodontic patient in accordance with an illustrative embodiment.

FIG. 4 depicts a side view of the dental/orthodontic assembly 200 of FIG. 2 being worn by a dental/orthodontic patient in accordance with an illustrative embodiment.

U.S. Provisional Application No. 62/329,513, filed Apr. 29, 2016, the entirety of which is hereby incorporated by reference herein for all purposes, in FIGS. 2-7 (the entirety which are incorporated by reference herein) includes photographs with additional details of an embodiment of a dental/orthodontic assembly as described with reference to FIGS. 2-4 of the present application being worn by a dental/orthodontic patient in accordance with an illustrative embodiment. U.S. Provisional Application No. 62/329,513 also includes claims (the entirety of which are incorporated by reference herein) which describe additional embodiments and arrangements of dental/orthodontic system and/or arrangements.

Various other modifications, adaptations, and alternative designs are of course possible in light of the above teachings. Therefore, it should be understood at this time that within the scope of the appended claims the disclosure may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method for providing a dental/orthodontic treatment comprising:

positioning a cervical collar on a patient such that that the cervical collar encircles the neck of the patient and restricts movement of the neck and/or head in at least one direction, the cervical collar comprising a brace with a mount, the brace coupled to a fixation point at an anterior section of the cervical collar positioned on a patient and the fixation point being positioned on the anterior section of the cervical collar below the chin of the patient, wherein the brace is configured to extend from the cervical collar in a direction of an oral cavity of the patient and wherein the brace is curved such that the brace extends from the anterior section of the collar below the chin of the patient and a middle section brace is positioned anterior to the anterior section of the collar below the chin;

engaging an upper support to a surface of a forehead of the patient, the support being secured to an upper end of the brace such that the middle section of the brace extends anterior to the support secured to the upper end of the brace; and coupling one or more elastics to the mount, wherein the one or more elastics are configured to extend from the mount to one or more oral fixation points within the oral cavity of the patient, wherein the one or more elastics are configured to exert a force on the one or more oral fixation points within the oral cavity of the patient.

2. The method of claim 1, wherein the mount is configured to slidably engage the brace, wherein the mount is configured to slide along a length of the brace when the mount is unsecured to the brace.

3. The method of claim 2, further comprising sliding the mount along the brace to a location adjacent to the oral cavity of the patient.

4. The method of claim 1, further comprising engaging a support to a surface of a forehead of the patient, the support being secured to an upper end of the brace.

5. The method of claim 4, wherein fixation of the brace to a fixation point at the anterior section of the cervical collar and engagement of the support to the surface of the forehead of the patient provide for fixation of the brace with respect to the patient in at least one direction.

6. The method of claim 4, wherein the brace curves from the support away from the forehead of the patient and towards a location adjacent to the oral cavity of the patient.

7. The method of claim 1, wherein fixing the brace to the fixation point at the anterior section of the cervical collar comprises fixing a lower end of the brace to a chin support of the cervical collar.

8. The method of claim 1, wherein the brace is curved.

9. The method of claim 8, wherein the brace curves from the fixation point at the anterior section of the cervical collar to a location adjacent to the oral cavity of the patient.

10. The method of claim 1 comprising coupling the mount to the brace.

11. The method of claim 1 wherein the cervical collar restricts flexion and extension of the neck.

\* \* \* \* \*